(12) United States Patent
Li et al.

(10) Patent No.: US 7,384,920 B2
(45) Date of Patent: Jun. 10, 2008

(54) USE OF STILBENE COMPOUNDS IN THE MANUFACTURE OF MEDICAMENT FOR THE PREVENTION AND TREATMENT OF DIABETES OR RETROVIRUS-ASSOCIATED DISEASES

(75) Inventors: Junlin Li, Beijing (CN); Zuze Wu, Beijing (CN); Lizhen Yuan, Beijing (CN); Qiang Li, Beijing (CN); Zhongxiong Tang, Beijing (CN)

(73) Assignees: Institute of Radiation Medicine, Academy of Military Medical Sciences, PLA, Beijing (CN); Beijing Luyin Lihua Pharmaceutical Science and Technology Development Company Ltd, Beijing (CN)

( * ) Notice: Subject to any disclaimer, the term of this patent is extended or adjusted under 35 U.S.C. 154(b) by 219 days.

(21) Appl. No.: 10/484,821

(22) PCT Filed: Jul. 26, 2001

(86) PCT No.: PCT/CN02/00522

§ 371 (c)(1),
(2), (4) Date: Sep. 2, 2004

(87) PCT Pub. No.: WO03/009838

PCT Pub. Date: Feb. 6, 2003

(65) Prior Publication Data

US 2005/0020511 A1    Jan. 27, 2005

(30) Foreign Application Priority Data

Jul. 26, 2001 (CN) ................................ 01 1 20597

(51) Int. Cl.
*A01N 43/04* (2006.01)
*A61K 31/70* (2006.01)
(52) U.S. Cl. .......................... 514/23; 514/25; 514/27; 514/724; 514/730; 514/738
(58) Field of Classification Search .................. 514/23, 514/25, 27, 724, 730, 738
See application file for complete search history.

(56) References Cited

U.S. PATENT DOCUMENTS

| 6,008,260 | A | * | 12/1999 | Pezzuto et al. ............. 514/733 |
| 6,197,834 | B1 | | 3/2001 | Docherty |
| 6,414,037 | B1 | * | 7/2002 | Pezzuto et al. ............. 514/733 |
| 6,448,450 | B1 | * | 9/2002 | Nag et al. ................... 568/646 |

FOREIGN PATENT DOCUMENTS

| CN | 1 196 245 | | 10/1998 |
| FR | 2 778 3371 | A1 | 11/1999 |
| JP | 61 171427 | A | 8/1986 |
| WO | WO-00/53176 | | 9/2000 |
| WO | WO-00/69430 | A1 | 11/2000 |
| WO | WO-01/42231 | A2 | 6/2001 |
| WO | WO-02/14252 | A | 2/2002 |

OTHER PUBLICATIONS

Hipskind et al., "Constitutive Accumulation of Resveratrol-Glucoside in Transgenic Alfalfa Increases Resistance to *Phoma medicaginis*", Molecular Plant-Microbe Interactions, 13(5), pp. 551-562, 2000.*
Zhongguo Zhongyao Zazhi, 1998, 23(8), p. 486-488, Min De et al, "studies on chemical constituents of *Rhemun wittrochii* Lundstr (II)", whole.
Arch-Pharm-Ber-Dtsch-Pharm-Ges. 1971, 304(1): Csupor-L, "Spectro-photometric determrmination of rhaponticin and desoxyrhaponticin in rhizoma *Rhei rhapontici* (L.)," title.
Zhongguo Yaolixue Yu Dulixue Zazhi, 1999, 13(1), Lu Sufang et a, "Advances in research on 3-4',5-trihydroxystilbene-3-beta-D-glucoside", abstract.
International Search Report.
Wang, Aiqin et al., "Blood Sugar Reducing Hydroxystibene Derivatives" (CN 1,294,912) Radiomedicine , Acad. of Military Medical Sciences of PLA, China May 16, 2001 Database Accession No. 2001:915350 (XP-002433173).
Manickam, M. et al., "Anthyperglycemic Activity Of Phenolics From *Pterocarpus marsupium*", Journal Nat. Prod., vol. 6, No. 60, Jun. 23, 1997, pp. 609-610 (XP001066243).
Ahn, K.S. et al. "Inhibitory Activity Of Stilbenes From Medicinal Plants On The Expression Of Cell Adhesion Molecules On THP1 Cells", Planta Medica, vol. 66, No. 7, Oct. 2000, pp. 641-644 (XP002433169).
Orsini F. et al., "Isolation Synthesis & Antiplatelet Aggregation Activity Of Resveratrol 3-0-SS-D-Glucopyranoside & Related Compounds", Journal of Nat. Prod., vol. 60, No. 1, 1997, pp. 1082-1087 (XP000914920).
Matsuda, H. H. et al., "Effects Of Stilbene Constituents From Rhubarb On Nitric Oxide Production In Lipopolysaccharide-Activated Macrophages", Bioorganic & Medicinal Chemistry Letters, vol. 10, No. 4, Feb. 2000, pp. 323-327 (XP004189924).
Cao, Zhiguo "Application Of Stilbene Phenol Glycoside Compound In Preparing The Blood Sugar-Lowering Medicine", CN 1,386,500, Dec. 25, 2002. Database Accession No. 2003:935090. (XP002433174).

* cited by examiner

*Primary Examiner*—Shaojia Anna Jiang
*Assistant Examiner*—Traviss C McIntosh, III
(74) *Attorney, Agent, or Firm*—Darby & Darby

(57) ABSTRACT

This invention relates to a new use of stilbene derivatives or pharmaceutically acceptable salts thereof, especially in the manufacture of medicament for the prevention and treatment of diabetes or retrovirus associated diseases.

1 Claim, No Drawings

USE OF STILBENE COMPOUNDS IN THE MANUFACTURE OF MEDICAMENT FOR THE PREVENTION AND TREATMENT OF DIABETES OR RETROVIRUS-ASSOCIATED DISEASES

This application is a § 371 national stage of International Application No. PCT/CN02/00522, filed Jul. 26, 2002, which was published in Chinese as International Publication No. WO 03/009838, and claims the benefit of priority of Chinese Patent Application No. 01120597.0, filed Jul. 26, 2001.

FIELD OF THE INVENTION

This invention relates to a new use of stilbene derivatives or pharmaceutically acceptable salts thereof, especially in the manufacture of medicament for the prevention and treatment of diabetes or retrovirus associated diseases.

TECHNOLOGY OF THE BACKGROUND

Diabetes is a common metabolic disorder in human beings. Recently, along with the improvement of living standard, and the changing of foodstuff structure, the incidence of diabetes are increasing rapidly. In the world there are around 0.12 billion of patients suffering from this disease. It is a serious threat to mankind. Therefore the prevention and treatment of diabetes is a hot focus in the field of medicinal research work.

Now the anti-diabetic medicament used in clinics such as sulfanylureas, biguanidins etc are effective yet with some side effects. Some formulation derived from Chinese traditional herbs are effective, less toxic. Up to now no hypoglycemic monomer derived from natural plants which is used in clinics is reported.

OBJECTION OF THE INVENTION

Objection of this invention is to develop a new use of stilbene derivatives or pharmaceutically acceptable salts thereof.

SUMMARY OF THIS INVENTION

The investigation of the inventors has discovered that the stilbene derivatives of formula I or pharmaceutically acceptable salts thereof have positive hypoglycemic effect and anti-retrovirus effect, then they could be useful for prevention and treatment of diabetes and retrovirus-associated diseases.

Therefore, the first aspect of this invention relates to a use of at least one stilbene derivatives of formula I or pharmaceutically acceptable salts thereof in the manufacture of medicament for the prevention and treatment of diabetes or retrovirus-associated diseases,

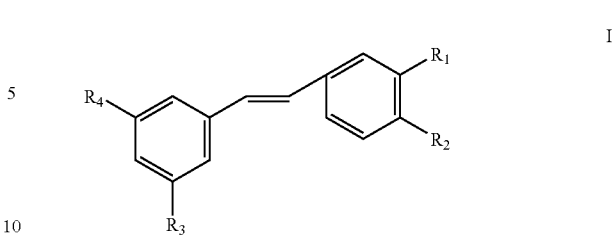

wherein, $R_1$, $R_2$, $R_3$ and $R_4$ are individually H, —OH, alkyl, $C_{6-10}$ aryl such as phenyl or naphthalenyl, alkylhydroxyl-, alkoxyl and sugar containing glycosides such as —O-glucosyl or -glucosyl.

The second aspect of this invention relates to a composition for the prevention and treatment of diabetes or retrovirus-associated diseases which comprising at least one stilbene derivatives of formula I or pharmaceutically acceptable salts thereof, pharmaceutically acceptable carrier or excipient,

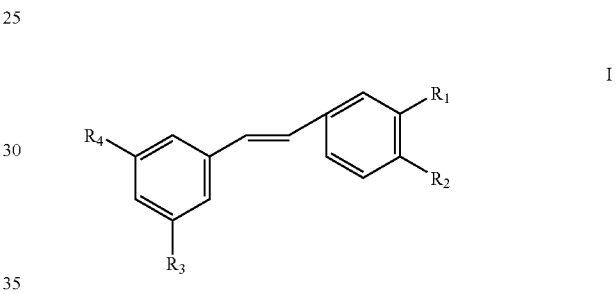

Wherein, $R_1$, $R_2$, $R_3$ and $R_4$ are independently H, —OH, alkyl, $C_{6-10}$ aryl such as phenyl or naphthalenyl, alkylhydroxyl-, alkoxyl and sugar containing glycosides such as —O-glucosyl or -glucosyl.

Furthermore, this invention relates to a method of the prevention and treatment of diabetes or retrovirus-associated diseases which comprising administrating a effective amount of stilbene derivatives of formula I or pharmaceutically acceptable salts thereof to the patient.

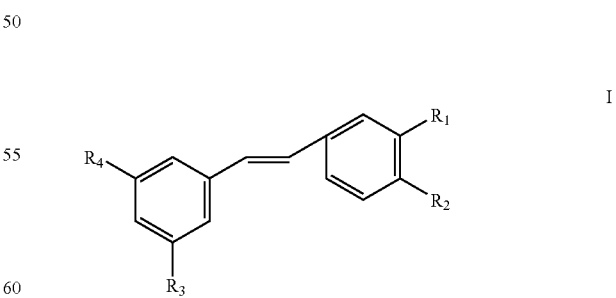

wherein $R_1$, $R_2$, $R_3$ and $R_4$ are independently H, —OH, alkyl, $C_{6-10}$ aryl such as phenyl or naphthalenyl, alkylhydroxyl-, alkoxyl and sugar containing glycosides such as —O-glucosyl or -glucosyl.

DETAILED DESCRIPTION OF THIS INVENTION

According to this invention, the compound derivatives of formula I may be obtained from a natural plants or by a chemical synthesis. For example, said compounds of formula I could be extracted from the natural plant such as *Vitis L, Ampelopsis Michx* of Vitaceae; *Arachis L, Cassia L, Sophora L*, of Leguminosae; *Veratrum L* of Liliaceae; *Eucalyptos L'H'erit* of Myrtaceae; and *Rheum emodi Wall, Rheum franzenbachii Munt, Rheum hotaoense C. Y. Chang, Rheum wittrockii Lundstr, Rhizoma polyoni cuspidati* of Polysonaceae According to this invention, the term "diabetes" used in this invention means to type I and for type II diabetes.

According to this invention, the term "patient" in this invention denotes mammalians such as human beings.

According to this invention, the term "alkyl group" denotes a lower alkyl containing 1-6 carbon atoms, the alkyl in terms "alkylhydroxyl group" or "alkoxyl" is defined as above definition of alkyl.

According to this invention, the retrovirus-associated diseases denote hepatitis or HIV infected diseases.

According to this invention, the preferred compounds of formula I in this invention are selected from:

3,4,5-trihydroxystilbene (compound E), 3,3',4',5-quadrahydroxystilbene-4'-O-β-D-glucopyranoside (Compound $E_1$)

3,4',5-trihydroxy-3'-methyloxy stilbene-3-O-β-D glucoside (compound $E_2$)

3,5-dihydroxy-4'-methyloxy stilbene-3-O-β-O-D glucoside (compound $E_3$)

3,4',5-trihydroxy stilbene-3'-O-D-glucoside (compound $E_5$)

According to this invention, stilbene derivatives of formula I may be formulated into to enteric or parenteral dosage forms such as tablet, capsule, granule or injection etc, by the known manner in the art.

Following examples will further illustrate this invention in detail but do not represent any limitation to the scope of the invention.

EXAMPLE 1

Preparation of 3,4,5-trihydroxystilbene (compound E)

Pour 95% alcohol to Huchan slices in proportion of 8:1 (V/W) was mixed and the obtained mixture was extracted for 3 cycles, 2 hrs per cycle, combining the extract solution, concentrating it in low pressure condition. The concentrated extract was dispersed by water, degreasing with ether, then extracting with ethyl acetate, n-butyl alcohol. The ethyl acetate fraction, n-butyl alcohol fraction and water fraction were obtained respectively. Separating ethyl acetate fraction on silica gel column (mash 60-100), compound E crude product was collected by ethyl acetate-methyl alcohol gradient elution, then re-crystallizing with acetone. N-butyl alcohol fraction was separated on silica column chromatography, with ethyl acetate gradient elution, compound $E_5$ product was collected, and re-crystallizing with acetone-water.

Identification:

Compound E is white needle crystal m.p.253-255° C., easily soluble in methyl alcohol, ethyl alcohol and acetone etc. $FeCl_3$ reaction shows green in color. Blue to violet fluorescence is excited by UV light.

Uvλ max MeOH (nm): 216,303.

IR(KBr)cm$^{-1}$: 3240,1880,1585,965.

$^1$HNMR(acetone-$d_6$)δppm: 8.79(1H,Br.s,4'-OH),8.48 (2H,Br.s,3,5-H),7.36(2H,dd,J=2.4/8.5 Hz,H-2',6'), 6.95(1H, d,J=16.2 Hz,H-β),6.81(1H,d,J=16.2 Hz,H-α),6.78(2H, dd,J=2.4/8.5 Hz,H-3'5'),6.77(2H, d,J=2.2 Hz,H-2,6),6.48 (1H,t,J=2.4 Hz,H-4).

$^{13}$CNMR(acetone-$d_6$)δppm: 159.47 (C-3,5),158.08(C-4'), 140.73(C-1),140.73(C-1),129.78(C-1'), 128.98(C-2',6'), 128.60(C-α),126.74(C-β), 116.29(C-3',5'), 105.47(C-2,6), 102.51(C-4).EI-MS m/z: 228($M^+$,100),227($M^+$-1),211($M^+$-OH),181,157,115,91,76.

Spectrum data is reported by Ming Te et al(1.Ming Te et al: Journal of Chinese traditional Medicine 1998,28(8):486) Therefore compound E is identified as 3,4,5-trihydroxystilbene or resveratrol.

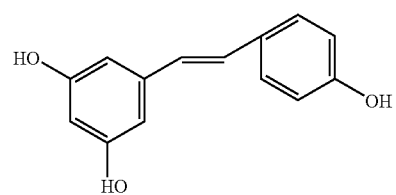

3,4,5-trihydroxystilbene or resveratrol.

EXAMPLE 2

Preparation of 3,3',4',5-quadrahydroxystilbene -4'-O-β-D-glucopyranoside (compound $E_1$)

Pour 95% ethyl alcohol to root and rhizome of Rheum emodi Wall in proportion of 8:1(V/W) was mixed, refluxed for 3 cycles, 2hr per cycle, combining the extract solution, concentrating in low pressure condition. The alcohol extract was dispersed by diatomite and drying.

Washing off lipid soluble fraction with chloroformn. Further elution with ethyl acetate, collecting soluble fraction. Separating this fraction by elution with ethyl acetate on silica gel chromatography (mash 60-100), then eluted with ethyl acetate/methanol (4:1-2), $E_1$ compound crude product was collected, and re-crystallizing with water-acetone.

Identification

Compound $E_1$ is white amorphous powder (diluted acetone)

m.p.138-140° C.

Blue to violet fluorescence was excited by UV light. Molisch reaction was positive.

$^1$HNMR(acetone-$d_6$)δppm: 7.14(1H,d,J=805 Hz,H-5'), 7.06(1 H,d,J=2.1 Hz,H-2'), 6.97(1H,d,J=16.3 Hz,H-β), 6.94 (1H,dd,J=2.1/8.5 Hz, H-6'),6.89(1H,d,J=16.3Hz, H-α),6.52 (2H,d,J=2.1 Hz,H-2,6),6.24(1H,t,J=2.1 Hz,H-4),4.79(1H,d, J=7.5 Hz,anome ric-H),3.9-3.3(sugar-H);

$^{13}$CNMR(acetone-$d_6$)δppm: aglycone 159.5(C-3,5),148.5 (C-4'), 146.0(C-3'),140.3(C-1),134.2(C-1'),128.6(C-α,β), 119.3 (C-5'), 118.9(C-6'), 114.2(C-2'),115.6(C-2,6),104.0(C-4),glucosyl: 102.9(C-1"),77.8(C-3"),77.1(C-5"),74.4(C-2"), 70.9(C-4"),62.2(C-6").

The 1HNMR and 13CNMR data are reported by Yoshiki Kashiwada et al (2 Yoshiki Kashiwada et al: Chem. Pharm Bull 1988,36(4):1545). Compound $E_1$ is identified as piceatannol-4'-O-β-D-glucopyranoside

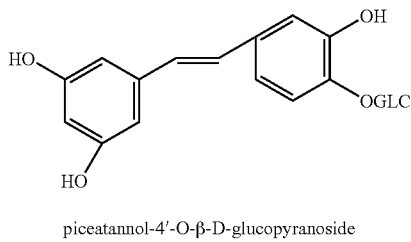

piceatannol-4'-O-β-D-glucopyranoside

EXAMPLE 3

Preparation of 3,4',5-trihydroxy-3'-methyloxy stilbene-3-O-β-D glucoside (compound $E_2$)

Compound $E_2$ was obtained from root and rhizome of *Rheum hotaoense* C. Y. Chang by the same procedure as to that in example 1 or example 2.

Identification:

Compound $E_2$ is while needle crystal (diluted methyl alcohol)

m.p.228-230° C.

Blue to violet fluorescence is excited by UV light. Molisch reaction is positive.

$^1$HNMR (acetone-$d_6$)δppm: 7.07(1H,d,J=2.0 Hz,H-2'), 7.02(1H,d,J=16.5Hz, H-β),6.96(1H,dd,J=2.0/8.3 Hz,H-6'), 6.90(1H,d,J=7.9 Hz, H-5'),6.89(1H,d,H=16.5 Hz,H-α),6.77 (1H,Br.s,H-2),6.66(1H,Br.s,H-2),6.48(1H,t,J=1.8 Hz,H-4), 4.90(1H,d,J=7.7 Hz,anomeric-H),3.82(3H,s, —OCH$_3$),4.0-3.3(sugar-H);

$^{13}$CNMR(acetone-$d_6$)δppm: aglycone 160.1 (C-5),159.5 (C-3), 148.4(C-4'),147.5(C-3'),140.5(C-1),131.5(C-1'), 129.5(C-β),127.2(C-α),119.7 (C-6'), 113.3(C-2'), 112.5(C-5'),108.0(C-2),106.5(C-6),103.8(C-4),56.2(—OCH$_3$);glucosyl: 101.9(C-1"), 77.7(C-3",5"),74.4(C-2"),71.1(C-4"), 62.5(C-6").

1HNMR and 13CNMR data are reported by Yoshiki Kashiwada et al (3 Yoshiki Kashiwada et al: Chem. Pharm Bull 1984.32(9): 3501), Compound $E_2$ was

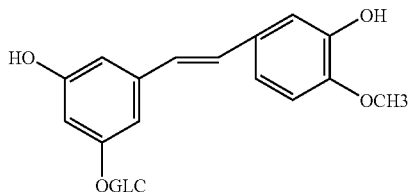

identified as 3,4',5-trihydroxy-3'-methyloxy stilbene-3-O-β-D-glucoside, or rhaponticin)

$E_2$ 3,4',5-trihydroxy-3'-methyloxy stilbene-3-O-β-D-glucoside, or rhaponticin

EXAMPLE 4

Preparation of 3,5-dihydroxy-4'-methyloxy stilbene-3-O-β-O-D glucoside (compound $E_3$) and 3,4',5-trihydroxy stilbene-3'-O-D-glucoside (compound $E_5$)

Compound $E_3$ or $E_5$ were obtained from root and rhizome of *Rheum franzenbachii* Munt or *Rhizoma polygoni* cuspidati by almost the same procedures as those in example 2.

Identification:

Compound $E_3$ is colorless needle crystal (acetone), m.p.210° C.,

Blue to violet fluorescence is excited by UV light. Molisch reaction is positive.

Uv λ max MeOH (nm): 216,296.IR(KBr)cm$^-$:3455,3320 (OH),1595,1505,830, 772,675.

$^1$HNMR(acetone-$d_6$)δppm: 7.51 (2H,d,J=8.6 Hz,H-2',6'), 7.08(1H,d,J=16.6 Hz,H-α), 6.94(1H,d,J=16.6 Hz,H-β),6.91 (1H,d,J=8.6 Hz,H-3',5'),6.70(2H,Br.s,H=2,6),6.35(1H,t, J=2.2 Hz,H-4),4.81 (2H,d,J=7.6 Hz,anomeric-H),3.76(3H,s, OCH$_3$),3.3-3.9(6H, m,sugar-H);

$^3$CNMR(acetone-$d_6$)δppm: 159.2(C-5),158.5(C-3),159.0 (C-4'), 139.0(C-1),129.2(C-1'),128.0(C-β),127.3(C-2',6'), 126.0(C-α),114.5(C-3'5'),107.2(C-6),104.8(C-2),103.0(C-4)55.2(OCH$_3$),glucosyl:101.8(C-1"),74.0(C-2"),77.2(C-3"), 70.8(C-4"),76.8(C-5"),61.8(C-6"). FAB-MS m/z: 404(M$^+$), 242(M$^+$-glu).

Above data is reported by Ming De et al (1 Ming De et al: Journal of Chinese traditional medicinal herbs,1998,23 (8): 486). Therefore $E_3$ is identified as 3,5-dihydroxy-4'-methyloxy stilbene-3-O-β-D-glucoside, or (desoxyrhaponticin)

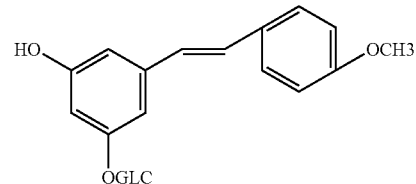

3,5-dihydroxy-4'-methyloxy stilbene-3-O-β-D-glucoside, or desoxyrhaponticin

Compound $E_5$ is white long needle crystal (acetone-water)

m.p.228-230° C., easily soluble in acetone.

Blue to violet fluorescence is excited by UV light. Molisch reaction is positive. Uv λ max MeOH (nm): 220, 303.

IR(KBr)cm$^1$:
3610,3310,2975,2923,2880,1610,1589,1516,1450,1360, 1320,1250,1170,1075,965, 840. $^1$HNMR(acetone-$d_6$)δppm: 8.89(1H,Br.s,4'-OH),8.86(1H,Br.s,5-OH),7.35(2H,dd,J=2.4/ 8.5 Hz,H-2',6'), 7.20(1H,d,J=16.2 Hz, H-β),6.84(1H,d, J=16.2 Hz,H-α),6.78(2H,dd,J=2.4/8.5 Hz,H-3'5'),6.73(1H, Br.s, H-6),6.62(1H,Br.s,H-2),6.45(1H,Br.s,H-4),4.88(1H,d, J=7.7 Hz,anomeric-H),3.8-3.2(sugar-H).

$^3$CNMR(acetone-d6)δppm: 160.10(C-3),159.33(C-5), 158.19(C-4'), 140.73(C-1),129.64(C-1'), 129.56(C-2',6'), 128.70(C-α),126.33(C-β), 116.31(C-3',5'), 108.00(C-2), 106.49(C-6),103.72(C-4),glucosyl: 101.90(C-1"),74.57(C-2"),77.76(C-3"),71.26(C-4"),77.64(C-5"),62.48(C-6"). FAB-MS m/z: 389($M^+$-H),242($M^+$-glu). .EI-MS m/z: 228 ($M^+$,100),227($M^+$-1),211($M^+$-OH),181,157,115,91,76.

The spectrum data is reported by Wang ZhenYu et al(4 Wang ZhenYu et al: Chinese herbs 1996,27(12): 714) Therefore $E_5$ is identified as 3,4',5-trihydroxy stilbene-3'-O-β-D-glucoside or ploydatin.

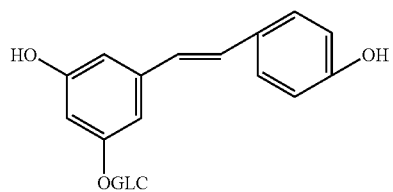

3,4',5-trihydroxy stilbene-3'-O-β-D-glucoside or ploydatin.

EXAMPLE 5

Biological Activity Assay

Following biological experiment demonstrated that the effect of the compounds in examples 1-5 on glucose tolerance curve of normal mice or on glucose levels of alloxan-induced diabetic mice. The metformin or miglucan were used as positive control drugs. And the hypoglycemic effects were evaluated. Hypoglycemic effect of stilbene derivatives on glucose level of alloxan induced diabetic mice.

KM strain male mice which have been fasted for 5-8 hours are used and be injected intravenously of alloxan 80mg/Kg, and 72 hours later, selected those with glucose level>11.0 mmol/L as the diabetic model mice for drug evaluation. Compounds were administered pos for 12 days. The results are shown in table 1:

TABLE 1

Hypoglycemic effect on glucose level of alloxan induced diabetic mice

| Compound | Group | Mice (no) | Dosage (mg/kg) | Predosing (mmol/L) | Postdosing (mmol/L) |
|---|---|---|---|---|---|
| E | Normal | 11 | $H_2O$ | 6.91 ± 1.01 | 7.31 ± 0.80 |
|  | Model | 11 | $H_2O$ | 17.30 ± 4.57 | 25.23 ± 9.17 |
|  | Metformin | 10 | 500 | 17.10 ± 4.84 | 15.16 ± 8.53 |
|  | E L | 11 | 150 | 17.87 ± 4.86 | 18.36 ± 6.25 |
|  | E S | 11 | 75 | 17.27 ± 4.60 | 20.01 ± 7.1 |
| $E_1$ | Normal | 11 | $H_2O$ | 7.14 ± 1.18 | 7.07 ± 1.32 |
|  | Model | 12 | $H_2O$ | 22.89 ± 3.94 | 22.95 ± 2.94 |
|  | Metformin | 13 | 500 | 22.81 ± 4.89 | 17.49 ± 5.33 |
|  | $E_1$ L | 13 | 1000 | 22.65 ± 3.55 | 16.54 ± 5.48 |
|  | $E_1$ M | 13 | 500 | 22.76 ± 3.17 | 16.39 ± 5.32 |
|  | $E_1$ S | 13 | 250 | 22.49 ± 4.63 | 21.10 ± 5.73 |
| $E_2$ | Normal | 8 | $H_2O$ | 7.12 ± 1.15 | 6.38 ± 1.53 |
|  | Model | 8 | $H_2O$ | 22.70 ± 4.33 | 27.79 ± 7.98 |
|  | Metformin | 8 | 500 | 21.15 ± 3.85 | 17.64 ± 1.00 |
|  | $E_2$ L | 8 | 1000 | 21.38 ± 5.75 | 24.64 ± 2.49 |
|  | $E_2$ M | 8 | 500 | 22.98 ± 5.94 | 28.96 ± 8.21 |
|  | $E_2$ S | 8 | 250 | 21.43 ± 5.04 | 22.61 ± 6.07 |
| $E_5$ | Normal | 11 | $H_2O$ | 6.91 ± 1.01 | 7.31 ± 0.80 |
|  | Model | 11 | $H_2O$ | 17.30 ± 4.57 | 25.23 ± 9.17 |
|  | Metformin | 10 | 500 | 17.10 ± 4.84 | 15.16 ± 8.53 |
|  | $E_5$ L | 11 | 150 | 17.92 ± 5.35 | 21.05 ± 4.63 |
|  | $E_5$ S | 11 | 75 | 17.46 ± 5.86 | 21.79 ± 9.39 |

Table 1 indicated that metoformin, positive control drug, is effective in the experiments, and the compounds of this invention E, $E_1$-$E_5$ are effective too, although some with higher or lower efficacy.

Effect of the Compounds of Examples 1-5 on Glucose Tolerance Curve of Normal Mice or Rats In these experiments, stilbene derivatives in examples 1-5 are administrated respectively to KM male mice or Wistar male rats pos for 12 days, then test animals were fasted for 8 hours, examined glucose values, and administrated the test compound. One hour later, administered ip of glucose 2 g/Kg (1.11 mol/L glucose solution). Determining the glucose values at 0, ½, 1, 2 hours after glucose injection and calculating the area under this glucose tolerance curve. The results are shown in table 2:

TABLE 2

Effect of E and E5 on glucose tolerance of normal rats (N = 6)

| Group | Dosage (mg/Kg) | Glucose (fasted) (mmol/L) | 0' | 30' | 60' | 120' | Auc |
|---|---|---|---|---|---|---|---|
| Normal | / | 5.4 ± 0.4 | 6.0 ± 0.8 | 12.5 ± 2.3 | 8.5 ± 1.7 | 6.6 ± 0.9 | 1044.2 ± 141.8 |
| Miglucan | 100 | 5.3 ± 0.7 | 3.4 ± 0.4 | 8.7 ± 3.5 | 5.3 ± 2.1 | 3.8 ± 1.4 | 663.8 ± 220.2 |
| E L | 150 | 5.8 ± 0.6 | 4.2 ± 0.4 | 9.5 ± 2.1 | 6.1 ± 1.2 | 4.7 ± 0.7 | 760.2 ± 119.6 |
| E S | 75 | 5.3 ± 0.9 | 4.9 ± 0.7 | 12.1 ± 2.3 | 7.5 ± 0.8 | 6.2 ± 0.9 | 961.1 ± 115.9 |
| Normal | / | 4.7 ± 0.8 | 5.2 ± 1.4 | 9.7 ± 0.5 | 6.5 ± 0.9 | 5.8 ± 0.8 | 853.1 ± 87.1 |
| Miglucan | 100 | 2.2 ± 0.2 | 2.7 ± 0.8 | 11.5 ± 0.6 | 7.8 ± 6.2 | 4.1 ± 1.7 | 883.1 ± 43.5 |
| $E_5$ L | 150 | 4.7 ± 0.8 | 4.3 ± 0.9 | 10.2 ± 1.5 | 6.3 ± 1.1 | 5.7 ± 1.1 | 836.3 ± 112.1 |
| $E_5$ S | 75 | 4.6 ± 0.5 | 4.9 ± 0.7 | 12.0 ± 1.5 | 7.4 ± 0.8 | 6.7 ± 0.7 | 966.8 ± 71.6 |

Table 2 indicated that compounds of this invention effectively stimulated the secretion of insulin in case of glucose loading. It is suggested that they can be useful for the treatment or prevention of type II diabetes Toxicity of compounds of this invention is shown in table 3.

TABLE 3

Maximal tolerance dose of the compounds of this invention in mice (pos)

| Compound | Sex of mice | MTD(g/kg) |
|---|---|---|
| E | ♀ | >6.10 |
|  | ♂ | >6.00 |
| $E_1$ | ♀ | 5.625 |
|  | ♂ | 4.219 |
| $E_2$ | ♀ | >16.872 |
|  | ♂ | >18.301 |
| $E_3$ | ♀ | >11.200 |
|  | ♂ | >11.000 |
| $E_5$ | ♀ | >10.00 |
|  | ♂ | >10.00 |

Table 3 indicated that the toxicity of compounds E, $E_1$, $E_2$, $E_3$ and $E_5$ is very low. According to acute toxicity classification proposed by WHO in 1977, they could be classified as low toxic or even no toxic agents.

And they are much less toxic than Metformin or miglucan used in clinics now.

Inhibition of Compounds of This Invention on HBeAg Expression

Experimental method: use 10% DMEM(with G418 380 μg/ml)to cultivate 2.2.15 cells, Add 1.5ml of $10^5$ cell/ml to 24 well plate for cultivation, change the new cultivate fluid next day and add different amount of compound to it, cultivate each concentration of compound to 3 wells, then collect and freeze 200 μl of supernatant of 2.2.15 cell culture at day 2,4,6 cultivation. Measure HBeAg value of the supernatant by ELISA. The results are shown in table 4:

TABLE 4

Inhibition of the compounds of this invention on expression of HBeAg 2.2.15 Cell($10^5$/ml)

| Compound | Day 2 OD | Day 2 IR (%) | Day 4 OD | Day 4 IR (%) | Day 6 OD | Day 6 IR (%) |
|---|---|---|---|---|---|---|
| $E_{1-2}$ | 0.244 | 57.75 | 0.208 | 32.68 | 0.228 | 51.57 |
| $E_{1-3}$ | 0.224 | 63.83 | 0.354 | −62.75 | 0.235 | 48.82 |
| $E_{2-2}$ | 0.199 | 71.43 | 0.188 | 45.75 | 0.251 | 56.69 |
| $E_{2-3}$ | 0.301 | 40.43 | 0.244 | 9.15 | 0.347 | 4.72 |
| $E_{3-2}$ | 0.194 | 72.95 | 0.197 | 39.87 | 0.177 | 71.65 |
| $E_{3-3}$ | 0.265 | 51.37 | 0.256 | 1.31 | 0.236 | 48.43 |
| 2.2.15 Ctr | 0.434 |  | 0.258 |  | 0.359 |  |

· $E_{1-2}$ and $E_{1-3}$ indicate compound E in concentration of 10 μg/ml and 20 μg/ml, $E_2$, $E_3$ are the same, OD optical density, IR inhibition rate, ctr control $E_3$ are the same, OD optical density, IR inhibition rate, ctr control IR=[Ctr(P/N)−Agent(P/N)]/[Ctr(P/N)−2.1]

Table 4 indicated that above compounds have inhibition activity on HBeAg expression.

What is claimed is:

1. A method for the treatment of diabetes or hepatitis B, comprising administering to a patient in need thereof an effective amount of at least one compound selected from:
3,3',4',5-quadrahydroxystilbene -4'-O-β-D-glucopyranoside,
3,4',5-trihydroxy-3'-methyloxy stilbene-3-O-β-D glucoside,
3,5-dihydroxy-4'-methyloxy stilbene-3-O-β-O-D glucoside,
3,4',5-trihydroxy stilbene-3'-O-D-glucoside; and
pharmaceutically acceptable salts thereof.

* * * * *

UNITED STATES PATENT AND TRADEMARK OFFICE
CERTIFICATE OF CORRECTION

PATENT NO. : 7,384,920 B2  Page 1 of 1
APPLICATION NO. : 10/484821
DATED : June 10, 2008
INVENTOR(S) : Junlin Li et al.

It is certified that error appears in the above-identified patent and that said Letters Patent is hereby corrected as shown below:

On the Title Page Item [22]:

Please delete "Jul. 26, 2001" and insert --July 26, 2002--

Signed and Sealed this

Twelfth Day of August, 2008

JON W. DUDAS
*Director of the United States Patent and Trademark Office*